United States Patent
Zhu et al.

(10) Patent No.: US 9,650,403 B2
(45) Date of Patent: May 16, 2017

(54) PLATINUM (II) COMPOUND, PREPARATION METHOD THEREFOR, AND PHARMACEUTICAL COMPOSITION AND APPLICATION THEREOF

(71) Applicants: SHANGHAI INSTITUTE OF PHARMACEUTICAL INDUSTRY, Shanghai (CN); CHINA STATE INSTITUTE OF PHARMACEUTICAL INDUSTRY, Shanghai (CN)

(72) Inventors: Baoquan Zhu, Shanghai (CN); Yongzhi Shu, Shanghai (CN); Jun Lin, Shanghai (CN); Haifeng Hu, Shanghai (CN); Quanhai Liu, Shanghai (CN); Bin Zhou, Shanghai (CN)

(73) Assignees: SHANGHAI INSTITUTE OF PHARMACEUTICAL INDUSTRY, Shanghai (CN); CHINA STATE INSTITUTE OF PHARMACEUTICAL INDUSTRY, Shnaghai (CN)

( * ) Notice: Subject to any disclaimer, the term of this patent is extended or adjusted under 35 U.S.C. 154(b) by 0 days.

(21) Appl. No.: 14/897,979

(22) PCT Filed: Mar. 19, 2014

(86) PCT No.: PCT/CN2014/073660
§ 371 (c)(1),
(2) Date: Dec. 11, 2015

(87) PCT Pub. No.: WO2014/198140
PCT Pub. Date: Dec. 18, 2014

(65) Prior Publication Data
US 2016/0194345 A1 Jul. 7, 2016

(30) Foreign Application Priority Data
Jun. 13, 2013 (CN) .......................... 2013 1 0234581

(51) Int. Cl.
| | | |
|---|---|---|
| *C07F 15/00* | (2006.01) | |
| *A61K 31/555* | (2006.01) | |
| *A61K 9/00* | (2006.01) | |
| *A61K 31/282* | (2006.01) | |
| *A61K 45/06* | (2006.01) | |

(52) U.S. Cl.
CPC ........ *C07F 15/0093* (2013.01); *A61K 9/0019* (2013.01); *A61K 31/282* (2013.01); *A61K 31/555* (2013.01); *A61K 45/06* (2013.01)

(58) Field of Classification Search
CPC .................................................. C07F 15/0093
See application file for complete search history.

(56) References Cited

FOREIGN PATENT DOCUMENTS

| | | |
|---|---|---|
| CN | 1683379 A | 10/2005 |
| CN | 923837 A | 3/2007 |
| JP | 59-222497 A | 12/1984 |

OTHER PUBLICATIONS

Howell et al. "The thermal degradation characteristics of selected organoplatinum antitumor agents" Journal of Thermal Analysis, 1993, vol. 40, pp. 395-403.*
First Office Action for related Chinese Patent Application No. 201410103727.2 dated Apr. 8, 2016.
English Translation of First Office Action for related Chinese Patent Application No. 201410103727.2 dated Apr. 8, 2016.
Second Office Action for related Chinese Patent Application No. 201410103727.2 dated May 30, 2016.
English Translation of Second Office Action for related Chinese Patent Application No. 201410103727.2 dated May 30, 2016.
International Search Report dated Jun. 11, 2014 issued in corresponding PCT/CN2014/073660 application.
(Continued)

*Primary Examiner* — Joseph Kosack
(74) *Attorney, Agent, or Firm* — Millen White Zelano and Branigan, PC; John Sopp; Anthony Zelano

(57) ABSTRACT

Disclosed are a platinum (II) compound, a preparation method therefor, and a pharmaceutical composition and an application thereof. The preparation method comprises the following steps: enabling dihydrate diammine platinum nitrate (4) to react with the carboxylate ligand derivative (5) in water, to produce a platinum (II) compound. Also provided are an application of the platinum (II) compound in preparation of an antitumor drug, and a pharmaceutical composition. The pharmaceutical composition contains an active component and a medicinal carrier, the active component containing the platinum (II) compound, and the mass percentage of the active component being 0.1%-95%. The platinum (II) compound of the present invention is well water-soluble, low toxic, easily prepared, and efficient in antitumor activity.

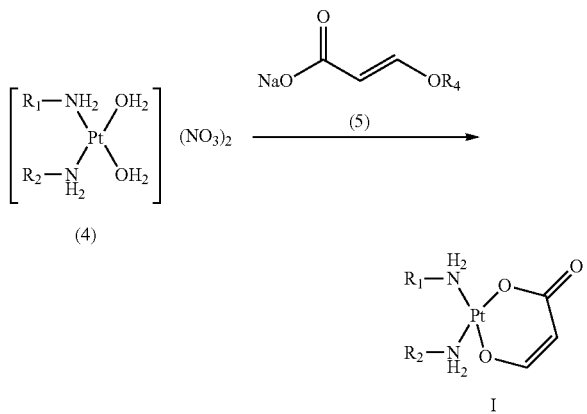

21 Claims, No Drawings

(56) References Cited

OTHER PUBLICATIONS

Written Opinion dated Jun. 11, 2014 issued in corresponding PCT/CN2014/073660 application (pp. 1-4).
Ye, Qing-Song et.al. "Synthesis and in vitro cytotoxicity of novel lipophilic (diamine)platinum (II) complexes of salicylate derivatives", Bioorganic & Medicinal Chemistry Letters, (Feb. 1, 2007), Issue 8, vol. 17, p. 2144-2147.
English Abstract for CN1683379, Publication Date: Oct. 19, 2005.
English Abstract for CN923837, Publication Date: Mar. 7, 2007.
English Abstract for JP59222497, Publication Date: Dec. 14, 1984.

\* cited by examiner

PLATINUM (II) COMPOUND, PREPARATION METHOD THEREFOR, AND PHARMACEUTICAL COMPOSITION AND APPLICATION THEREOF

CROSS REFERENCE TO RELATED APPLICATION

The present application is the U.S. national stage application of International Application PCT/CN2014/073660, filed Mar. 19, 2014, which international application was published on Dec. 18, 2014, as International Publication WO2014/198140. The International Application claims priority of Chinese Patent Application 201310234581.0, filed Jun. 13, 2013, the contents of which are incorporated herein by reference in their entireties.

FIELD OF INVENTION

The present invention relates to a biopharmaceuticals field, specifically relates to a platinum (II) compound, a preparation method therefor, and a pharmaceutical composition and a use thereof.

PRIOR ARTS

Cisplatin has been widely used in the clinic treatment of various kinds of solid tumors as an antineoplastic drug since it was discovered, and it has significant efficacy in the treatment of genitourinary cancer, nasopharyngeal cancer, head and neck cancer, lung cancer and other cancers. However, the serious toxicity caused by Cisplatin, such as nephrotoxicity, neurotoxicity, ototoxicity and gastrointestinal disorders, limit its doses and long-term medication. As a second generation of the platinum anticancer drug, Carboplatin (also known as carboplatinum) has a similar anticancer spectrum to Cisplatin and is with lower toxic, but the efficacy of which is worse, the cross-resistance and bone marrow suppression of which are remained. Therefore, it is still a hot spot of research and development domestically and overseas to seek for a platinum anticancer drug with high activity and low toxicity.

It has been reported that a variety of platinum anticancer drugs are used for clinical trials in recent years, such as Zeniplatin, Sebriplatin, Ormaplatin, Iproplatin, JM-20, PHIC and so on. However, those new platinum compounds were failed to be used clinically due to poor water solubility, no broader antineoplastic spectrum available since the same cancer strains are inhibited as Cisplatin, and high toxicity etc.

Nonetheless, the research on modifying and improving the platinum compounds to develop an anticancer drug is never stopped, since its unique anticancer mechanism, broad anticancer spectrum, and different toxicity spectrum from natural and organically synthesized drugs.

Patent (JP showa 59-222497) discloses Nedaplatin (glycolato-cis-diammine platinum (II)), a platinum derivative, with anticancer effects, the structure of which is quite different from the present invention. The present invention opens up a whole new field, which is of great significance.

CONTENT OF THE PRESENT INVENTION

The technical problem to be solved in the present invention is to overcome the defects of the anticancer drugs derived from the platinum compounds in the prior art, such as the poor water solubility, high toxicity, narrow anticancer spectrum, to provide a platinum (II) compound, a preparation method therefor, and a pharmaceutical composition and a use thereof. The platinum (II) compound in the present invention is well water-soluble, low-toxic, easily prepared, and high efficient in antitumor activity.

The present invention provides a platinum (II) compound represented by Formula I having a structure as follows,

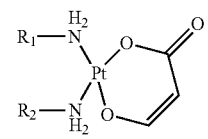

I wherein, each of $R_1$ and $R_2$ is independently a hydrogen or a hydroxyl which is substituted by a $C_{1-12}$ hydrocarbyl; alternatively, $R_1$ and $R_2$ are linked with a bond and together with the carbon atoms to which they are attached form a saturated or unsaturated carbon ring with 3-12 ring atoms.

$R_1$ is preferably a hydrogen.

$R_2$ is preferably a hydrogen.

The $C_{1-12}$ hydrocarbyl defined in $R_1$ and $R_2$ is preferably a $C_{1-6}$ hydrocarbyl.

The saturated or unsaturated carbon ring with 3-12 ring atoms defined in $R_1$ and $R_2$ is preferably a saturated or unsaturated carbon ring with 4-8 ring atoms, more preferably a saturated carbon ring with 6 ring atoms.

The platinum (II) compound represented by Formula I is preferably wherein, both $R_1$ and $R_2$ are hydrogen;

alternatively, $R_1$ and $R_2$ are linked with a bond and together with the carbon atoms to which they are attached form a saturated carbon ring with 3-8 ring atoms (preferably a saturated carbon ring with 6 ring atoms).

The platinum (II) compound represented by Formula I is more preferably cis-3-hydroxy-acrylic acid diammine platinum (II); or cis-3-hydroxy-acrylic acid (trans-(−)-1,2-diaminocyclohexane) platinum (II) (6).

The platinum (II) compound represented by Formula I is most preferably cis-3-hydroxy-acrylic acid diammine platinum (II) (2).

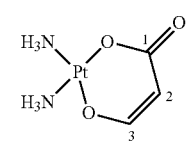

(2)

The present invention also provides a method for preparing the above platinum (II) compound represented by Formula I, comprising: reacting a dihydrate diammine platinum nitrate (4) and a carboxylate ligand derivative (5) in water to produce the platinum (II) compound represented by Formula I;

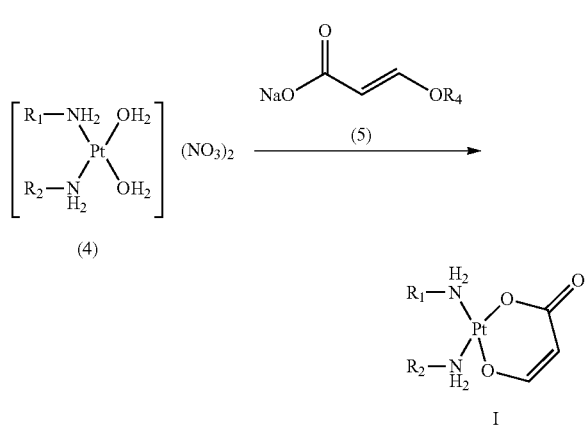

wherein, each of $R_1$ and $R_2$ is independently a hydrogen or a hydroxyl which is substituted by a $C_{1-12}$ hydrocarbyl; alternatively, $R_1$ and $R_2$ are linked with a bond and together with the carbon atoms to which they are attached form a saturated or unsaturated carbon ring with 3-12 ring atoms;

$R_4$ is a hydrogen or a $C_{1-12}$ hydrocarbyl.

$R_1$ is preferably a hydrogen.

$R_2$ is preferably a hydrogen.

The $C_{1-12}$ hydrocarbyl defined in $R_1$ and $R_2$ is preferably a $C_{1-6}$ hydrocarbyl.

The saturated or unsaturated carbon ring with 3-12 ring atoms defined in $R_1$ and $R_2$ is preferably a saturated or unsaturated carbon ring with 4-8 ring atoms, more preferably a saturated carbon ring with 6 ring atoms.

$R_4$ is preferably a $C_{1-6}$ hydrocarbyl. The $C_{1-6}$ hydrocarbyl is preferably an ethyl.

The platinum (II) compound represented by Formula I is preferably wherein, both $R_1$ and $R_2$ are hydrogen;

alternatively, $R_1$ and $R_2$ are linked with a bond and together with the carbon atoms to which they are attached form a saturated carbon ring with 3-8 ring atoms (preferably a saturated carbon ring with 6 ring atoms).

More preferably, the platinum (II) compound represented by Formula I is cis-3-hydroxy-acrylic acid diammine platinum (II); or cis-3-hydroxy-acrylic acid (trans-(-)-1,2-diaminocyclohexane) platinum (II).

The platinum (II) compound represented by Formula I is most preferably cis-3-hydroxy-acrylic acid diammine platinum (II) (2).

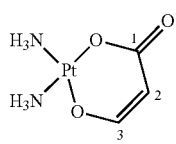

The carboxylate ligand derivative (5) is preferably sodium 3-ethoxyacrylate.

The method for preparing the platinum (II) compound represented by Formula I preferably comprises: mixing an aqueous solution of the dihydrate diammine platinum nitrate (4) and an aqueous solution of the carboxylate ligand derivative (5) at 30 to 80° C., keeping the mixture away from light and reacting.

In the method for preparing the platinum (II) compound represented by Formula I, a mole ratio of the dihydrate diammine platinum nitrate (4) to the carboxylate ligand derivative (5) is preferably 1 to (1-2).

In the method for preparing the platinum (II) compound represented by Formula I, an amount of water should generally meet the requirement for not affecting the process of the reaction, which is preferably 50-150 ml/g relative to the dihydrate diammine platinum nitrate (4).

In the method for preparing the platinum (II) compound represented by Formula I, a mass concentration of the aqueous solution of the carboxylate ligand derivative (5) is preferably 10-500 ml/g, more preferably 50-100 ml/g.

In the method for preparing the platinum (II) compound represented by Formula I, the reaction is preferably at 40 to 70° C., more preferably at 60 to 65° C.

In the method for preparing the platinum (II) compound represented by Formula I, the process of the reaction can be monitored by HPLC or TLC, generally the completion of the reaction is determined when the reactant (4) disappears. The reaction generally costs 2 to 24 hours, preferably 3 to 8 hours.

After the reaction for preparing the platinum (II) compound represented by Formula I finishes, the prepared platinum (II) compound represented by Formula I can be further purified by post-treating. The post-treating preferably comprising: filtering the reaction system, concentrating until solid precipitates, cooling, filtering, washing and drying. The washing is preferably with cool water and anhydrous ethanol respectively. The temperature of the drying is preferably 40 to 70° C. The concentrating is preferably under vacuum. The conditions and steps of the vacuum concentration can be the conventional conditions and steps in the art. The vacuum concentration is preferably at 45 to 50° C.

In the method for preparing the platinum (II) compound represented by Formula I, the method for preparing the dihydrate diammine platinum nitrate (4) preferably comprising: reacting a compound represented by Formula (3) and silver nitrate in water while keeping the reaction away from light to produce the dihydrate diammine platinum nitrate (4);

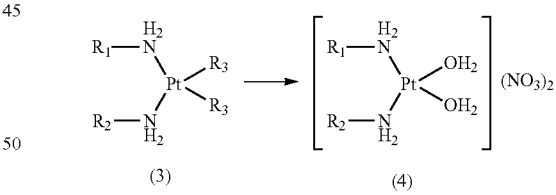

wherein, $R_3$ is I or Cl; $R_1$ and $R_2$ are as defined above.

The method for preparing the compound represented by Formula (4) preferably comprises: mixing an aqueous solution of the compound represented by Formula (3) and an aqueous solution of the silver nitrate, keeping the mixture away from light and reacting at 10 to 100° C.

In the method for preparing the compound represented by Formula (4), a mole ratio of the compound represented by Formula (3) to the silver nitrate is preferably 1 to (1-2).

In the method for preparing the compound represented by Formula (4), an amount of water should generally meet the requirement for not affecting the process of the reaction, which is preferably 50-150 ml/g relative to the compound represented by Formula (3).

In the method for preparing the compound represented by Formula (4), the concentration of the aqueous solution of the silver nitrate is preferably 15-60 ml/g relative to silver nitrate.

In the method for preparing the compound represented by Formula (4), the reaction is preferably at 40 to 70° C., more preferably at 50 to 55° C.

In the method for preparing the compound represented by Formula (4), the process of the reaction can be monitored by HPLC or TLC, generally the completion of the reaction is determined when the reactant (3) disappears. The reaction generally costs 2 to 24 hours, preferably 3 to 8 hours.

After the reaction for preparing the compound represented by Formula (4) finished, the reaction system is preferably filtered, and the filtrate is directly used for the preparation of the platinum (II) compound represented by Formula I.

When the reaction for preparing the compound represented by Formula (4) finishes, the filtrate is directly used for the preparation of the platinum (II) compound represented by Formula I, the steps of which preferably comprise: mixing the filtrate and the carboxylate ligand derivative (5) at 30 to 80° C., and keeping the reaction away from light to produce the platinum (II) compound represented by Formula I.

In the present invention, one preferred reaction route is as follows:

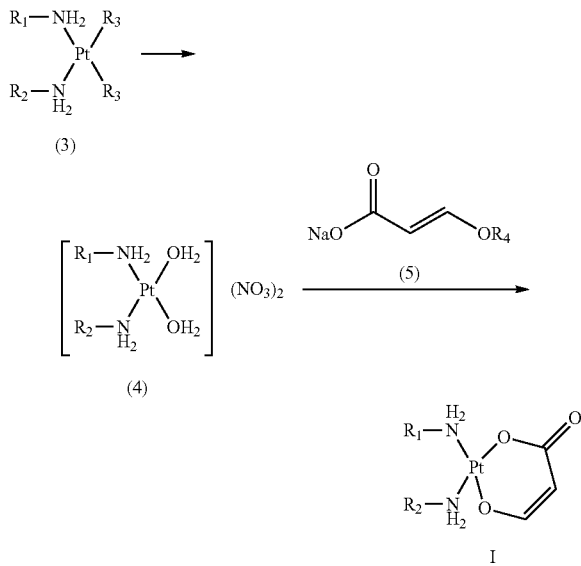

The present invention also provides a use of the platinum (II) compound represented by Formula I in preparing an antitumor drug.

The platinum (II) compound represented by Formula I in the present invention is suitable for being used to prepare an antitumor drug for mammal, in particular an antineoplastic agent for human.

Specifically, the platinum (II) compound represented by Formula I in the present invention has therapeutic activity against a variety of human tumors, such as renal carcinoma, hepatic carcinoma, esophageal carcinoma, gastric cancer, bladder carcinoma, breast carcinoma, ovarian carcinoma, colon cancer, prostate carcinoma, pancreatic carcinoma, lung cancer, thyroid carcinoma, myoma, vagina carcinoma, cervical cancer, glioblastoma, head-neck cancer (including nasal cavity neoplasms, paranasal sinus neoplasms, laryngopharynx and cervical esophageal neoplasms, oropharyngeal neoplasms, thyroid neoplasms), leukemia and malignant lymphoma.

The present invention also provides a pharmaceutical composition, comprising an active component and a pharmaceutically acceptable carrier, the active component comprising the platinum (II) compound represented by Formula I, wherein a mass of the active component accounts for 0.1%-95% of a total mass of the pharmaceutical composition.

In the pharmaceutical composition, the platinum (II) compound represented by Formula I is preferably cis-3-hydroxy-acrylic acid diammine platinum (II); or cis-3-hydroxy-acrylic acid (trans-(−)-1,2-diaminocyclohexane) platinum (II); more preferably cis-3-hydroxy-acrylic acid diammine platinum(II) (2).

A method for preparing the pharmaceutical composition can be a conventional method in the art, particularly 'The Technology of Modern Pharmaceutical' (Qi peng Yuan, Chemical Industry Press, the first edition, 2005) is for reference.

The method for preparing the pharmaceutical composition preferably comprises: mixing the active component and the pharmaceutically acceptable carrier.

The pharmaceutical composition can be an injection preparation.

The pharmaceutically acceptable carrier can include the carrier selected from the group consisting of an inert diluent agent, water and an organic solvent.

In the pharmaceutical composition, the active component can also comprise at least one other antineoplastic drug. When the active component comprises at least one other antineoplastic drug, the pharmaceutical composition can be administered by administering each of the active component simultaneously, sequentially, periodically or separately.

In the present invention, the term "$C_{1-12}$ hydrocarbyl" refers to a functional group only comprising carbon atom and hydrogen atom, wherein the number of the carbon atom is 1 to 12. The hydrocarbyl can be regarded as a radical derived from its corresponding hydrocarbon which loses a hydrogen atom, such as an alkyl, a cycloalkyl, an alkenyl or an alkynyl etc. The structure of the hydrocarbyl can be a linear chain, a branched chain or a ring.

The definition of the term "$C_{1-6}$ hydrocarbyl" is the same as the term "$C_{1-12}$ hydrocarbyl", the only difference is that the number of the carbon atom is 1 to 6.

The definition of the term "$C_{1-3}$ hydrocarbyl" is the same as the term "$C_{1-12}$ hydrocarbyl", the only difference is that the number of the carbon atom is 1 to 3.

In the present invention, the term "carbon ring" refers to a saturated or unsaturated ring only comprising carbon atoms, which can be substituted by any conventional substituent in the art. The 'carbon ring' can be a cycloalkyl (such as cyclohexyl etc.), a cycloalkenyl or a cycloalkynyl.

In the present invention, the mentioned optimized conditions can be optionally combined without departing from the general knowledge in this field to obtain preferred embodiment.

In the present invention, the involved reactions are usually under atmosphere.

In the present invention, the reagents and raw materials can be commercially available or prepared according to the prior art.

The positive effects achieved by the present invention are that the platinum (II) compound represented by Formula I in the present invention are well water-soluble and with high anticancer activity.

DETAILED DESCRIPTION OF THE PREFERRED EMBODIMENT

The present invention was further described by the embodiments, but the scope of the present invention is not intended to be limited by the following embodiments. In the following embodiments, the experimental methods without specific conditions, can be carried on by conventional methods and conditions or according to the commodity instruction.

Example 1

The preparation of cis-3-hydroxy-acrylic acid diammine platinum (II)

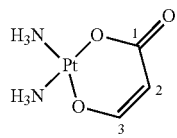

(2)

1) 1.0 g 3-ethoxy-acrylic acid was dissolved in 100 mL pure water, and a solution of sodium hydroxide (containing 0.34 g NaOH) was added to adjust a pH value to neutral. The reaction mixture was concentrated to dryness and a yellow product was given. The yellow product was filtered, washed with water and ethanol respectively and dried to obtain sodium 3-ethoxyacrylate 1.15 g, the yield is 97.1%.

2) cis-diammine diiodo platinum (II) ($(NH_3)_2PtI_2$) 4.16 g was dissolved in 300 mL pure water, and an aqueous solution of silver nitrate 50 mL (containing 2.92 g $AgNO_3$) was added. The mixture was stirred, reacted at 50° C. for 4 h while kept away from light, and then filtered. The filtrate was added slowly into 100 mL aqueous solution of sodium 3-ethoxyacrylate (containing 1.15 g sodium 3-ethoxyacrylate). The mixture was reacted at 65° C. for 4 h while kept away from light, and then filtered. The filtrate was concentrated under reduced pressure to 15 mL at 45° C. White precipitation was precipitated, filtered, and the precipitation was washed respectively with cool pure water and anhydrous ethanol for 2 times, and dried at 60° C. to obtain cis-3-hydroxy-acrylic acid diammine platinum (II) 1.10 g, the water-solubility of which is greater than 25 mg/mL (at room temperature) and the yield is 40.5%.

The cis-3-hydroxy-acrylic acid diammine platinum (II) represented by Formula (2) prepared according to the above example 1 was white amorphous powder, the structure of which was determined by MS, elemental analysis, NMR, IR etc.

The ESI-MS of the cis-3-hydroxy-acrylic acid diammine platinum (II) is m/z: 316 $[M+H]^+$, the molecular weight is 315, the HR-ESI-MS is m/z: 316.0263 $[M+H]^+$ and the calculated molecular formula is $C_3H_8N_2O_3Pt$.

The result of the elemental analysis of C, H, N comprised in the cis-3-hydroxy-acrylic acid diammine platinum (II) is as follows:

Calculated value (%): C, 11.43; H, 2.56; N, 8.89.
Measured value (%): C, 10.93; H, 2.98; N, 8.54.
The NMR data of the cis-3-hydroxyacrylic acid diammine platinum (II):

TABLE 1

| position | $\delta_H$ (mult, J, Hz) | $\delta_C$ (mult) |
|---|---|---|
| 1 | — | 165.8 |
| 2 | 4.14 (1H, d, 6) | 95.7 |
| 3 | 6.55 (1H, d, 6) | 164.7 |
| $NH_3$ | 3.92 (3H, brs) | — |
| $NH_3$ | 3.86 (3H, brs) | — |

In table 1, the hydrogen in position 1, 2 and 3 respectively represents the marked hydrogen in the structure of the compound represented by Formula (2).

The analysis of the IR of the cis-3-hydroxy acrylic acid diammine platinum (II) ($cm^{-1}$ KBr):
3284 strong band is N—H stretching vibration band
1584 strong band is C═O stretching vibration band
1521 strong band is C═C stretching vibration band
1287 strong band is C—N stretching vibration band
1437 strong band is C—H bending vibration band
1347 strong band is C—O stretching vibration band.

Example 2

The preparation of cis-3-hydroxy-acrylic acid diammine platinum (II)

1) 2.0 g 3-ethoxyacrylic acid was dissolved in 100 mL pure water, and a solution of sodium hydroxide (containing 0.68 g NaOH) was added to adjust a pH value to neutral. The reaction mixture was concentrated to dryness and a yellow product was given. The yellow product was filtered, washed with water and ethanol respectively and dried to obtain sodium 3-ethoxyacrylate 2.31 g, and the yield is 97.5%.

2) cis-diammine diiodo platinum (II) ($(NH_3)_2PtI_2$) 4.16 g was dissolved in 450 mL pure water, and an aqueous solution of silver nitrate 20 mL (containing 2.92 g $AgNO_3$) was added. The mixture was stirred, reacted at 52° C. for 4 h while kept away from light, and then filtered. The filtrate was added slowly into 100 mL aqueous solution of sodium 3-ethoxyacrylate (containing 2.31 g sodium 3-ethoxyacrylate). The mixture was reacted at 70° C. for 4.5 h while kept away from light, and then filtered. The filtrate was concentrated under reduced pressure to 15 mL at 55° C. White precipitation was precipitated, filtered, and the precipitation was washed respectively with cool pure water and anhydrous ethanol for 2 times, and dried at 60° C. to obtain cis-3-hydroxy acrylic acid diammine platinum (II) 1.16 g, the yield is 45.1%.

Example 3

The preparation of cis-3-hydroxy-acrylic acid (trans-(−)-1,2-diaminocyclohexane) platinum (II)

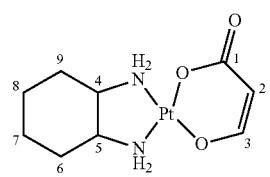

(6)

1) 1.0 g 3-ethoxyacrylic acid was dissolved in 100 mL pure water, and a solution of sodium hydroxide (containing 0.34 g NaOH) was added to obtain a solution of sodium 3-ethoxyacrylate, and then a pH value was adjusted to neutral. The reaction mixture was concentrated to dryness and a yellow product was given. The yellow product was filtered, washed with water and ethanol respectively and dried to obtain sodium 3-ethoxyacrylate 1.16 g, the yield is 97.5%.

2) 3.40 g cis-diiodo-(trans-(−)-1,2-diaminocyclohexane) platinum (II) was dissolved in 300 mL pure water, and a solution of silver nitrate (containing 1.46 g $AgNO_3$) was added. The mixture was stirred, reacted at 55° C. for 5 h while kept away from light, and then filtered. The filtrate was added into 100 mL aqueous solution of sodium 3-ethoxyacrylate (containing 1.16 g sodium 3-ethoxyacrylate). The mixture was reacted at 60° C. for 5 h while kept away from light, and then filtered. The filtrate was concentrated under reduced pressure to 15 mL at 50° C. and a crude product was given. The crude product was purified through a reversed-phase silica gel (40 g, $AQ-C_{18}$) and eluted by a mixture of methanol:water=10:90 (volume ratio). The eluent was collected and concentrated under reduced pressure at 50° C. to dryness and a white solid was given. The white solid was dried at 60° C. to obtain a pure cis-3-hydroxy-acrylic acid (trans-(−)-1,2-diaminocyclohexane) platinum (II) 0.766 g, the water-solubility of which is greater than 20 mg/mL (at room temperature), and the yield is 32.1%.

Structure characteristic parameters of cis-3-hydroxy-acrylic acid (trans-(−)-1,2-diaminocyclohexane) platinum (II) is:

ESI-MS m/z: 396.09 $[M+H]^+$. The measured value of elemental analysis: C, 26.95%; H, 4.05%; N, 6.97% was consistent with the calculated value of elemental analysis: C, 27.34%; H, 4.08%; N, 7.09%. The NMR data was shown in table 2. According to the above parameters, the structure of the compound in the present invention was determined.

TABLE 2

| position | $\delta_H$ (mult, J, Hz) |
| --- | --- |
| 2 | 4.24 (1H, d, 6) |
| 3 | 6.68 (1H, d, 6) |
| 4, 5 | 2.13 (2H, S) |
| 6a, 9b | 1.46 (2H, d, 8) |
| 6b, 9a | 1.81 (2H, d, 11.2) |
| 7a, 8b | 1.20 (2H, d, 9.2) |
| 7b, 8a | 1.00 (2H, t) |
| $NH_3$ | 3.92 (3H, brs) |
| $NH_3$ | 3.86 (3H, brs) |

In table 2, the hydrogen atoms in position 2, 3, 4, 5, 6a, 6b, 7a, 7b, 8a, 8b, 9a and 9b correspond to the hydrogen atoms in the marked positions in the structure of the compound represented by Formula (6) respectively, wherein, 6a and 6b corresponds to the two hydrogen atoms in the marked position 6. Similarly, 7a and 7b, 8a and 8b, 9a and 9b respectively represent the two hydrogen atoms in the marked position 7, 8, 9 in the structure of the compound represented by Formula (6).

Example 4

The preparation of cis-3-hydroxy-acrylic acid (trans-(−)-1,2-diaminocyclohexane) platinum (II)

1) 1.4 g 3-ethoxyacrylic acid was dissolved in 80 mL pure water, and a solution of sodium hydroxide (containing 0.48 g NaOH) was added to obtain a solution of sodium 3-ethoxy-acrylate, and a pH value was adjusted to neutral. The reaction mixture was concentrated to dryness and a yellow product was given. The yellow product was filtered, washed with water and ethanol respectively and dried to obtain sodium 3-ethoxyacrylate 1.60 g, the yield is 96.5%.

2) 3.40 g cis-diiodo-(trans-(−)-1,2-diaminocyclohexane) platinum (II) was dissolved in 300 mL pure water, and a solution of silver nitrate (containing 1.46 g $AgNO_3$) was added. The mixture was stirred, reacted at 50° C. for 5 h while kept away from light, and then filtered. The filtrate was added into 100 mL aqueous solution of sodium 3-ethoxyacrylate (containing 1.60 g sodium 3-ethoxyacrylate). The mixture was reacted at 40° C. for 8 h while kept away from light, and then filtered. The filtrate was concentrated under reduced pressure to 15 mL at 50° C. and a crude product was given. The crude product was purified through a reversed-phase silica gel (40 g, $AQ-C_{18}$) and eluted by a mixture of methanol:water=10:90 (volume ratio). The eluent was collected and concentrated under reduced pressure at 50° C. to remove the solvent and a white solid was given. The white solid was dried at 60° C. to dryness and then pure cis-3-hydroxyacrylic acid (trans-(−)-1,2-diamino cyclohexane-) platinum (II) 0.730 g, and the yield is 30.5%.

Effect Example 1

An antineoplastic experiment in vitro was carried out with cis-3-hydroxy-acrylic acid diammine platinum (II).

MTT method was employed to test the cytotoxic effect caused by the compound on human tumor cell stains in vitro. Specific steps are as follows:

The tumor cells (human poorly differentiated gastric cancer cell stain BGC-823, human breast cancer cell strain Bcap37, human oral cancer cell strain KB) was cultured in a 10% calf serum, inoculated into a 96-well plate ($2\times10^5$ cells per well) at 37° C. in an incubator with 5% $CO_2$. The cis-3-hydroxy-acrylic acid diammine platinum (II) was dissolved in DMSO to obtain a solution with a concentration of 10 mg/ml. The solution was diluted to the required concentration with a phosphate buffer, and then added into the wells of the 96-well plate respectively, each concentration was for two wells, 10 μl per well, therefore, each concentration has two parallel tests. DMSO was diluted accordingly in a gradient manner and added into the wells of the 96-well plate as controls.

After the 96-well plate was kept at 37° C. in the incubator with 5% $CO_2$ for 48 hours, 20 μl 5 mg/ml MTT solution was added into per well. Then the 96-well plate were further kept for 3-4 hours in the incubator at the same temperature. 100 μl solvent was added into per well and the 96-well plate was kept warm in the incubator overnight to make the generated formazan crystals dissolve sufficiently. The light absorption value at 492 nm was determined.

A relative survival rate of cells was calculated according to the light absorption value after the treatment of the compound. The calculation formula is as follows:

$$\text{The relative survival rate of cells} = \frac{\text{the light absorption value of the group treated by the compound} - \text{the light absorption value of the background}}{\text{the light absorption value of the group treated by DMSO} - \text{the light absorption value of the background}} \times 100$$

The IC$_{50}$ of the compound against each kind of tumor cells was calculated though software.

The effects of cis-3-hydroxy-acrylic acid diammine platinum (II) on inhibiting proliferation of various tumor cell strains in vitro are shown in table 1:

TABLE 1

| Cell strains | IC$_{50}$ (μg/ml) |
|---|---|
| BGC-823 | 2.28 |
| KB | 33.94 |
| Bcap37 | 21.58 |

The above results indicated that the platinum (II) compound represented by Formula I, in particular cis-3-hydroxy-acrylic acid diammine platinum (II), has a good activity of inhibiting tumor cells.

Effect Example 2

An antineoplastic experiment was carried out in vivo with cis-3-hydroxyacrylic acid diammine platinum (II).

The model of ICR mice with transplanted 5180 sarcoma in vivo was used to determine the anticancer effect of the compound. Specific steps are as follows:

1) Experimental Samples

Samples: cis-3-hydroxy-acrylic acid diammine platinum (II), serial number: SIPI-601.

Positive control: Oxaliplatin for injection, Jiangsu Hengrui Medicine Co., Ltd, lot number: 13082811, 50 mg per bottle.

2) Preparation Method

Samples: SIPI-601, which was dissolved by a 10% glucose injection.

Positive control: Oxaliplatin for injection, which was dissolved by a 10% glucose injection.

3) Animals and Tumor Cell Strains

32 ICR mice, male, weight 18-20 g, were supplied by Sippr/Bk Laboratory Animals Ltd, certification: SCXK (shanghai) 2008-2016.

Tumor cell trains: two ICR mice with S180 ascites tumor, passage cultured by pharmacological office, Shanghai State Institute of Pharmaceutical Industry (SIPI).

4) Experimental Method

The ascites of two vigorous growing ICR mice with S180 ascites tumor was extracted under a sterile condition, diluted 6 times with saline water, axilla subcutaneously inoculated with a dosage of 0.2 ml per mouse. The mice were randomly divided into four groups the next day, 8 for each group.

The groups were blank control group, SIPI-601 60 mg/kg iv group (administered once every three days), SIPI-601 120 mg/kg iv group (administered once every six days), Oxaliplatin 9 mg/kg iv group (administered once every other day).

The mice were administered the second day after inoculation. The dosages and methods of administration were shown in the table below. After the treatment, the survived animals were euthanatized, the tumors were taken and weighed to calculate anti-tumor rate.

$$\text{anti-tumor rate} = \frac{\text{tumor weight of control group} - \text{tumor weight of administered group}}{\text{tumor weight of control group}} \times 100\%$$

5) Experimental Results

The anti-tumor rate of the sample SIPI-601 with which the ICR mice with transplanted S180 tumor were administered intravenously were shown in table 2:

| group | The initial body weight (g) | The final body weight after the removal of tumor(g) | The anti-tumor rate (%) |
|---|---|---|---|
| blank | 22.81 | 24.56 | — |
| SIPI-601 (60 mg/kg iv) | 22.21 | 22.46 | 64.39 |
| SIPI-601 (120 mg/kg iv) | 22.78 | 20.34 | 66.83 |
| Oxaliplatin (9 mg/kg iv ) | 23.18 | 19.92 | 62.42 |

The above results indicated that the platinum (II) compound represented by Formula I, in particular cis-3-hydroxy-acrylic acid diammine platinum (II) represented by Formula (2), has a good activity against tumor in vivo.

What is claimed is:

1. A platinum (II) compound represented by Formula I having a structure as follows,

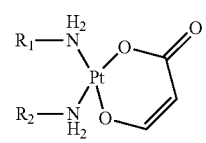

I wherein, each of R$_1$ and R$_2$ is independently a hydrogen or a hydroxyl which is substituted by a C$_{1-12}$ hydrocarbyl; alternatively, R$_1$ and R$_2$ are linked with a bond and together with the carbon atoms to which they are attached form a saturated or unsaturated carbon ring with 3-12 ring atoms.

2. The platinum (II) compound represented by Formula I defined as claim 1, wherein the C$_{1-12}$ hydrocarbyl defined in R$_1$ and R$_2$ is a C$_{1-6}$ hydrocarbyl; the saturated or unsaturated carbon ring with 3-12 ring atoms defined in R$_1$ and R$_2$ is a saturated or unsaturated carbon ring with 4-8 ring atoms.

3. The platinum (II) compound represented by Formula I defined as claim 2, wherein the saturated or unsaturated carbon ring with 4-8 ring atoms defined in R$_1$ and R$_2$ is a saturated carbon ring with 6 ring atoms.

4. The platinum (II) compound represented by Formula I defined as claim 1, wherein the platinum (II) compound represented by Formula I is cis-3-hydroxy-acrylic acid diammine platinum (II); or cis-3-hydroxy-acrylic acid (trans-(−)-1,2-diaminocyclohexane) platinum (II).

5. A method for preparing the platinum (II) compound represented by Formula I defined as claim 1, comprising: reacting a dihydrate diammine platinum nitrate (4) and a carboxylate ligand derivative (5) in water to produce the platinum (II) compound represented by Formula I;

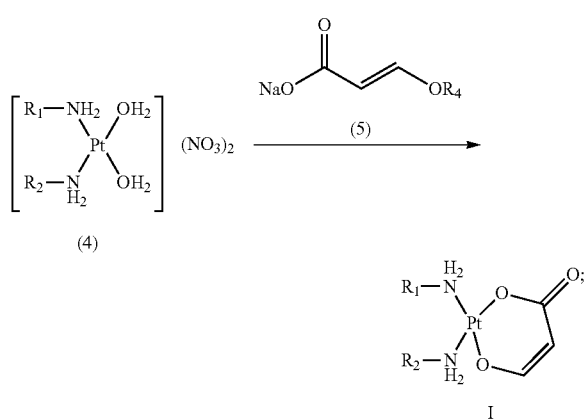

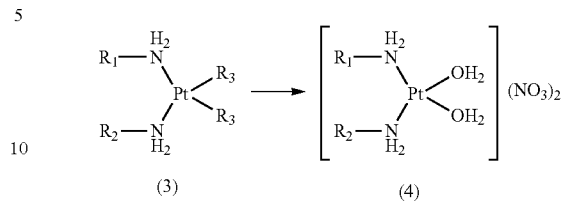

wherein, each of $R_1$ and $R_2$ is independently a hydrogen or a hydroxyl which is substituted by a $C_{1-12}$ hydrocarbyl; alternatively, $R_1$ and $R_2$ are linked with a bond and together with the carbon atoms to which they are attached form a saturated or unsaturated carbon ring with 3-12 ring atoms;

$R_4$ is a hydrogen or a $C_{1-12}$ hydrocarbyl.

6. The method for preparing the platinum (II) compound represented by Formula I defined as claim 5, wherein $R_4$ is a $C_{1-6}$ hydrocarbyl.

7. The method for preparing the platinum (II) compound represented by Formula I defined as claim 6, wherein the $C_{1-6}$ hydrocarbyl defined in $R_4$ is an ethyl.

8. The method for preparing the platinum (II) compound represented by Formula I defined as claim 5, wherein the carboxylate ligand derivative (5) is sodium 3-ethoxyacrylate.

9. The method for preparing the platinum (II) compound represented by Formula I defined as claim 5, comprising: mixing an aqueous solution of the dihydrate diammine platinum nitrate (4) and an aqueous solution of the carboxylate ligand derivative (5) at 30 to 80° C., keeping the mixture away from light and reacting.

10. The method for preparing the platinum (II) represented by Formula I defined as claim 9, wherein
   in the method for preparing the platinum (II) compound represented by Formula I, a mole ratio of the dihydrate diammine platinum nitrate (4) to the carboxylate ligand derivative (5) is 1 to (1-2);
   in the method for preparing the platinum (II) compound represented by Formula I, an amount of water is 50-150 ml/g relative to the dihydrate diammine platinum nitrate (4);
   in the method for preparing the platinum (II) compound represented by Formula I, a mass concentration of the aqueous solution of the carboxylate ligand derivative (5) is 10-500 ml/g;
   in the method for preparing the platinum (II) compound represented by Formula I, the reaction is at 40 to 70° C.

11. The method for preparing the platinum (II) compound represented by Formula I defined as claim 10, wherein
   in the method for preparing the platinum (II) compound represented by Formula I, the mass concentration of the aqueous solution of the carboxylate ligand derivative (5) is 50-100 ml/g;
   in the method for preparing the platinum (II) compound represented by Formula I, the reaction is at 60 to 65° C.

12. The method for preparing the platinum (II) compound represented by Formula I defined as claim 5, comprising: reacting a compound represented by Formula (3) and silver nitrate in water while keeping the mixture away from light to produce the dihydrate diammine platinum nitrate (4);

wherein $R_3$ is I or Cl; each of $R_1$ and $R_2$ is independently a hydrogen or a hydroxyl which is substituted by a $C_{1-12}$ hydrocarbyl; alternatively, $R_1$ and $R_2$ are linked with a bond and together with the carbon atoms to which they are attached form a saturated or unsaturated carbon ring with 3-12 ring atoms.

13. The method for preparing the platinum (II) compound represented by Formula I defined as claim 12, wherein the method for preparing the dihydrate diammine platinum nitrate (4) comprising: mixing an aqueous solution of the compound represented by Formula (3) and an aqueous solution of the silver nitrate, and reacting at 10 to 100° C. while keeping the mixture away from light.

14. The method for preparing the platinum (II) compound represented by Formula I defined as claim 12, wherein
   in the method for preparing the dihydrate diammine platinum nitrate (4), a mole ratio of the compound represented by Formula (3) to the silver nitrate is 1:(1-2);
   in the method for preparing the dihydrate diammine platinum nitrate (4), an amount of water is 50-150 ml/g relative to the compound represented by Formula (3);
   in the method for preparing the dihydrate diammine platinum nitrate (4), the reaction temperature is 40 to 70° C.

15. The method for preparing the platinum (II) compound represented by Formula I defined as claim 13, wherein
   in the method for preparing the dihydrate diammine platinum nitrate (4), the concentration of the aqueous solution of the silver nitrate is 15-60 ml/g relative to silver nitrate.

16. The method for preparing the platinum (II) compound represented by Formula I defined as claim 14, wherein in the method for preparing the dihydrate diammine platinum nitrate (4), the reaction temperature is 50 to 55° C.

17. The method for preparing the platinum (II) compound represented by Formula I defined as claim 12, wherein after the reaction for preparing the dihydrate diammine platinum nitrate (4) finished, the reaction system is filtered and the filtrate is directly used for the preparation of the platinum (II) compound represented by Formula I;
   when the reaction for preparing the dihydrate diammine platinum nitrate (4) finished and the filtrate was directly used for the preparation of platinum (II) compound represented by Formula I, the method for preparing the platinum (II) compound represented by Formula I comprises: mixing the filtrate and the carboxylate ligand derivative (5) at 30 to 80° C., and then reacting while keeping the mixture away from light to produce the platinum (II) compound represented by Formula I.

18. A method of treating tumor in a subject in need thereof, comprising: administer an effective amount of the platinum (II) compound represented by Formula I defined as claim 1 to the subject.

19. A pharmaceutical composition, comprising an active component and a pharmaceutically acceptable carrier, the active component comprising the platinum (II) compound represented by Formula I defined as claim 1, wherein a mass of the active component accounts for 0.1%-95% of a total mass of the pharmaceutical composition.

20. The pharmaceutical composition defined as claim 19, wherein the pharmaceutical composition is an injection preparation; the pharmaceutically acceptable carrier includes the carrier selected from the group consisting of an inert diluent agent, water and an organic solvent.

21. The pharmaceutical composition defined as claim 19, wherein the active component also comprises at least one other antineoplastic drug.

* * * * *